United States Patent
Pijls et al.

(10) Patent No.: US 11,963,743 B2
(45) Date of Patent: Apr. 23, 2024

(54) SYSTEM AND METHOD FOR DETERMINING THE MICROVASCULAR RESISTANCE RESERVE

(71) Applicant: Coroventis Research AB, Uppsala (SE)

(72) Inventors: Nico H. J. Pijls, Waalre (NL); Bernard De Bruyne, Kraainem (BE)

(73) Assignee: Coroventis Research AB, Uppsala (SE)

( * ) Notice: Subject to any disclaimer, the term of this patent is extended or adjusted under 35 U.S.C. 154(b) by 0 days.

(21) Appl. No.: 18/002,808

(22) PCT Filed: May 31, 2021

(86) PCT No.: PCT/SE2021/050504
§ 371 (c)(1),
(2) Date: Dec. 21, 2022

(87) PCT Pub. No.: WO2021/262062
PCT Pub. Date: Dec. 30, 2021

(65) Prior Publication Data
US 2023/0225622 A1 Jul. 20, 2023

(30) Foreign Application Priority Data
Jun. 22, 2020 (SE) .................................. 2030208-9

(51) Int. Cl.
*A61B 5/02* (2006.01)
*A61B 5/0215* (2006.01)
*A61B 5/055* (2006.01)

(52) U.S. Cl.
CPC ...... *A61B 5/02028* (2013.01); *A61B 5/02007* (2013.01); *A61B 5/0215* (2013.01); *A61B 5/055* (2013.01)

(58) Field of Classification Search
None
See application file for complete search history.

(56) References Cited

U.S. PATENT DOCUMENTS

| 9,408,541 B2 | 8/2016 | Kuri | |
|---|---|---|---|
| 2013/0246034 A1* | 9/2013 | Sharma | G16H 50/50 703/11 |

(Continued)

FOREIGN PATENT DOCUMENTS

| CN | 111166317 A | 5/2020 |
|---|---|---|
| EP | 2942006 A1 | 11/2015 |

(Continued)

OTHER PUBLICATIONS

"Cardiovascular Medicine", Swiss Society of Cardiology, 2020;23 (Suppl. 28).

(Continued)

*Primary Examiner* — Meredith Weare
(74) *Attorney, Agent, or Firm* — Servilla Whitney LLC

(57) ABSTRACT

The invention relates to a method for determining the microvascular resistance reserve, MRR, in the myocardium perfused by a normal or a stenotic coronary artery of a human patient, which method comprises the step of during rest condition of the patient: measuring the blood flow, $Q_{rest}$, through the coronary artery; and further comprising the step of during rest condition or during maximum hyperemia of the patient: measuring the blood pressure, $P_a$, at a position proximal in the coronary artery or proximally of any stenosis, if present; and further comprising the steps of during maximum hyperemia of the patient: measuring the blood flow, $Q_{max}$, through the coronary artery; and measuring the blood pressure, $P_d$, at a position distal in the coronary artery or distally of any stenosis, if present, and wherein the microvascular resistance reserve, MRR, is determined by the additional step of calculating the microvascular resistance reserve as $$MRR = \frac{Q_{max}}{Q_{rest}} \frac{P_a}{P_{d,hyper}}.$$

24 Claims, 4 Drawing Sheets

(56) References Cited

U.S. PATENT DOCUMENTS

| | | | | |
|---|---|---|---|---|
| 2015/0324962 A1* | 11/2015 | Itu | ............................ | G06T 7/00 |
| | | | | 382/130 |
| 2021/0212565 A1* | 7/2021 | Gardner | ............... | A61B 5/0024 |
| 2021/0244293 A1* | 8/2021 | Belleville | .............. | G16H 50/30 |
| 2021/0321888 A1* | 10/2021 | Morris | ................... | A61B 34/10 |
| 2021/0361170 A1* | 11/2021 | Schwartz | ........... | A61B 5/02152 |
| 2022/0184067 A1* | 6/2022 | Berry | ........................ | A61P 9/10 |
| 2023/0307144 A1* | 9/2023 | He | ........................ | G16H 50/50 |
| | | | | 600/300 |

FOREIGN PATENT DOCUMENTS

| | | |
|---|---|---|
| KR | 101753576 B1 | 7/2017 |
| WO | 2016112049 A1 | 7/2016 |
| WO | 2020000102 A1 | 1/2020 |
| WO | 2020165226 A1 | 8/2020 |

OTHER PUBLICATIONS

English Machine Translation of CN111166317A.
English Machine Translation of KR101753576B1.
PCT International Preliminary Report on Patentability in PCT/SE2021/050504 dated Sep. 5, 2022, 12 pages.
Candreva, A., et al., "Quantifying coronary microvascular disease: assessing absolute microvascular resistance reserve (MRR) by continuous coronary thermodilution", Cardiovascular Medicine (abstracts), SSC, p. 40, Jun. 5, 2020.

* cited by examiner

SYSTEM AND METHOD FOR DETERMINING THE MICROVASCULAR RESISTANCE RESERVE

CROSS-REFERENCE TO RELATED APPLICATIONS

This application is a National Phase entry of International Application No. PCT/SE2021/050504, filed May 31, 2021, which claims priority to Swedish Patent Application No. 2030208-9, filed Jun. 22, 2020, the disclosures of which are incorporated herein by reference in their entireties.

FIELD OF THE INVENTION

The present invention relates generally to assessment of the coronary circulation of the heart of a human patient, and relates more specifically to methods and systems for determining the microvascular resistance reserve and the microvascular resistance of the coronary microcirculation in the heart.

BACKGROUND OF THE INVENTION

The coronary circulation, i.e. the blood supply of the heart, consists of the so-called epicardial coronary arteries, which have a diameter in the interval of about 0.5 to 5 millimeter and are visible on a coronary angiogram, and the so-called coronary microcirculation or microvasculature, which consists of arterioles and capillaries having a diameter less than 0.5 millimeter and are not visible on a coronary angiogram.

Disease of the epicardial coronary arteries, e.g. narrowings or occlusions, which can lead to angina pectoris or heart attacks, can be well diagnosed and treated by multiple techniques. In all patients diagnosed with a coronary artery disease, 25-50% of the patients suffer, however, from symptoms which are not caused solely by epicardial narrowings but also by microvascular disease. Reliable systems and techniques for assessing such a complex disease are unfortunately not yet available. Instead present methods are crude, inaccurate, operator-dependent, and are not quantitative or do not discriminate between the contributions of the epicardial arteries and the microvasculature to the disease. Without the possibility to distinguish between epicardial contribution and microvascular contribution to a disease, optimum diagnosis and treatment of patients having a heart disease is apparently hampered.

In an article by Xaplanteris et al. (*Circ Cardiovasc Interv.* 2018; 11:e006194. DOI: 10.1161/CIRCINTERVENTIONS. 117.006194), it is shown how the absolute microvascular resistance at maximum hyperemia can be derived from measurements of blood pressure and maximum blood flow. Knowledge of the absolute microvascular resistance solves some of the problems mentioned above, but so far absolute microvascular resistance can only be assessed during maximum vasodilation of the microvasculature, and its use is further limited by the lack of uniform normal values due to large variation depending on the amount of myocardial tissue being perfused and a large variation within normal, i.e. healthy, individuals.

The object of the present invention is therefore to provide an improved method and a system for assessment of microvascular coronary disease, which, in turn, will facilitate and improve the diagnosis and treatment of the microvascular coronary disease in question. Another object of the invention is to provide an improved method and a system for assessment of microvascular coronary disease in presence of also epicardial coronary disease.

SUMMARY OF THE INVENTION

The above-mentioned objects are achieved by the present invention according to the independent claims. Preferred embodiments are set forth in the dependent claims.

The method and system according to the invention include calculation of microvascular resistance under resting conditions in such a manner that it is not confounded by the presence of epicardial disease, and provide a new index, called microvascular resistance reserve (MRR), which unequivocally measures the microvascular function or the severity of microvascular disease, not confounded by the presence of epicardial disease. To obtain MRR, measurements under both resting and hyperemic conditions are performed.

Herein, the terms "proximal" and "distal" as well as similar or related terms such as "proximally", "distally", "proximal position", "proximal pressure", "distal position" and "distal pressure" are used. These are well-known and generally accepted definitions within the field of cardiology and also in the cardiovascular scientific literature. In case of a coronary stenosis, whether focal or diffuse and revealed or detected by, e.g., coronary angiography or FFR measurement, the term "proximal" refers to a position proximal to that stenosis and the term "distal" refers to a position distal to that stenosis. In case of a normal or near-normal coronary artery, the term "proximal" refers to a position in the first part of that artery, i.e. close to its ostium, and the term "distal" refers to a position in the distal part of the coronary artery. In FIG. 1, a stenotic artery is schematically depicted to illustrate the description of the invention, but also without a stenosis, i.e. in the case of a normal coronary artery, the description and scope of the present invention remain valid with "proximal" and "distal" pressures as defined above. Thus, wherever, the expression "position proximal of any stenosis" is used, one should read "proximal in the coronary artery" in the case that there is no epicardial stenosis present, i.e. in case of a normal coronary artery; and wherever the expression "position distal of any stenosis" is used, one should read "distal in the coronary artery" in the case that there is no epicardial stenosis present, i.e. in case of a normal coronary artery, where "any" also can be "a" or "the" or similar determinations.

Pressure measured at a position proximal in the coronary artery or proximally of any stenosis, if present, is indicated by $P_a$. If $P_a$ is measured under resting conditions, it is called $P_{a,rest}$ and if it is measured under hyperaemic conditions, it is called $P_{a,hyper}$.

Pressure measured at a position distal in the coronary artery or distally of any stenosis, if present, is indicated by $P_d$. If $P_d$ is measured under resting conditions, it is called $P_{d,rest}$ and if it is measured under hyperaemic conditions, it is called $P_{d,hyper}$.

The microvascular resistance reserve, MRR, is defined as:

$$MRR = \frac{R_{micro,rest}}{R_{micro,min}}$$

where $R_{micro,rest} = P_{a,rest}/Q_{rest}$, and $R_{micro,min} = P_{d,hyper}/Q_{max}$, It should be realized that the actual resting microvascular resistance measured for any myocardial territory is influenced by the presence of epicardial disease. The latter, whether focal or diffuse, will lead to compensatory microvascular vasodilation by autoregulation. Thus, measured microvascular resistance is not the true $R_{micro,rest}$ but a lower value due to the autoregulatory compensation. Accordingly, it is noteworthy to emphasize that $R_{micro,rest}$ as used here does not represent the actually present resting microvascular resistance but the value of resting microvascular resistance in the (hypothetical) case that the epicardial conduit is completely normal. $Q_{rest}$ is the blood flow through the coronary artery during rest and $Q_{max}$ is the blood through the coronary artery during hypermia.

All six aspects of the invention described below are based on the common inventive concept that they are based on a microvascular resistance during rest, $R_{micro,rest}$, which is not confounded by epicardial disease. $R_{micro,rest}$ may also be called true microvascular resistance at rest because it is not dependent on epicardial disease, if present.

In a first aspect, the invention relates to a method for determining the microvascular resistance reserve, MRR, in the myocardium perfused by a normal or a stenotic coronary artery of a human patient, which method comprises the step of during rest condition of the patient:
measuring the blood flow, $Q_{rest}$, through the coronary artery; and further comprising the step of during rest condition or during maximum hyperemia of the patient:
measuring the blood pressure, $P_a$, at a position proximal in the coronary artery or proximally of any stenosis if present; and further comprising the steps of during maximum hyperemia of the patient:
measuring the blood flow, $Q_{max}$, through the coronary artery; and
measuring the blood pressure, $P_{d, hyper}$, at a position distal in the coronary artery or distally of any stenosis if present, wherein
the microvascular resistance reserve, MRR, is determined by the additional step of calculating the microvascular resistance reserve as $$MRR = \frac{Q_{max}}{Q_{rest}} \frac{P_a}{P_{d,hyper}}.$$

In one embodiment of the invention, the blood pressure ($P_a$) measured proximal in the coronary artery or proximally of any stenosis if present comprises the step of measuring the aortic blood pressure.

In a second aspect, the invention relates to a system for determining the microvascular resistance reserve, MRR, in the myocardium perfused by a normal or a stenotic coronary artery of a human patient, which system comprises:
a processing unit;
a first flow measuring system configured for measuring the blood flow, $Q_{rest}$, through the coronary artery during rest condition of the patient;
a first pressure measuring instrument configured for measuring the blood pressure, $P_a$, at a position proximal in the coronary artery or proximally of any stenosis, if present, during rest condition or during maximum hyperemia of the patient;
a second flow measuring system configured for measuring the blood flow, $Q_{max}$, through the coronary artery during maximum hyperemia of the patient; and
a second pressure measuring instrument configured for measuring the blood pressure, $P_{d, hyper}$, at a position distal in the coronary artery or distally of any stenosis, if present, during maximum hyperemia of the patient,
wherein the processing unit is configured for obtaining blood flow measurements $Q_{rest}$, $Q_{max}$ from the first and second flow measuring systems and obtaining blood pressure measurements $P_a$, $P_d$ from the first and second pressure measuring instruments, and wherein the processing unit is further configured for calculating the microvascular resistance reserve as $$MRR = \frac{Q_{max}}{Q_{rest}} \frac{P_a}{P_{d,hyper}}$$

As described above, the first and second aspects of the invention comprise measuring the blood pressure, $P_a$, at a position proximal in the coronary artery or proximally of any stenosis, if present, either during rest condition or during maximum hyperemia of the patient. It is noted that the calculation of MRR is only correct if the numerical value of $P_a$ equals $P_{a,rest}$, i.e. $P_a$ measured during rest condition. In other words, when determining MRR, the measured value of $P_a$ measured during maximum hyperemia may only be used if using techniques for inducing a hyperemic state in a patient such that aortic pressure is generally independent of the state of the patient (rest/hypermia). The two different embodiments for measuring $P_a$ (during rest or hypermia) are described below.

In embodiments of the first or second aspect of the invention, the blood pressure at a position proximal in the coronary artery or proximally of any stenosis, if present, is measured during rest condition of the patient, to obtain $P_{a, rest}$. In such an embodiment, the microvascular resistance reserve is calculated as $$MRR = \frac{Q_{max}}{Q_{rest}} \frac{P_a}{P_{d,hyper}}.$$

$P_{a,rest}$ may be determined by means of any known invasive or non-invasive technique. The general invasive technique to measure $P_{a, rest}$ is by means of the coronary (guide) catheter. The simplest non-invasive technique comprises measuring the aortic blood pressure using a sphygmomanometer ("cuff measurement").

In alternative embodiments of the first or second aspect of the invention, where the blood flows are measured using techniques such that aortic pressure is generally independent of the state of the patient (rest/hypermia), the blood pressure at a position proximal in the coronary artery or proximally of any stenosis, if present, may instead be measured during maximum hypermia of the patient, to obtain $P_{a, hyper}$. In such an embodiment, the microvascular resistance reserve is calculated as $$MRR = \frac{Q_{max}}{Q_{rest}} \frac{P_{a,rest}}{P_{d,hyper}}, \text{ where } P_{a,rest} = P_{a,hyper}.$$

In one embodiment, the microvascular resistance, $R_{micro, rest}$, at rest condition of the patient is calculated as $R_{micro, rest} = P_{a, rest}/Q_{rest}$.

In embodiments of the first or second aspect of the invention, the blood flow measurements conducted to obtain $Q_{rest}$, $Q_{max}$ and the pressure measurement to obtain $P_{d, hyper}$ are performed at different times. For example, the blood flows can be obtained during a first exam, and $P_{d, hyper}$ can be obtained during a separate second exam, such as an invasive cardiac catheterization performed at a different time or by noninvasive FFR determination (by CT). In such case, the knowledge that $P_{d, hyper}/P_{a, hyper}$ is constant and not depending on the moment when it is measured, enables combination of (separately assessed) $P_{d, hyper}$ (whether invasively by a pressure wire or non-invasively by CT) and the respective blood flow measurements measured at another moment and this provides MMR. $P_a$ may be measured during the same exam as the blood flow measurements by means of a sphygmomanometer ("cuff measurement").

The microvascular resistance reserve (MRR) as defined above has the unique property of being specific for microvascular disease without being influenced by the presence or absence of epicardial disease.

In one embodiment of the invention, the first flow measuring system and the second flow measuring system are the same flow measuring system.

In one embodiment the system further comprises a display unit configured for receiving the calculated value of the microvascular resistance reserve from the processing unit and displaying said calculated value.

In one embodiment of the system, the first pressure measuring instrument is a pressure or guiding catheter; and in another embodiment, the first pressure measuring instrument and/or the second pressure measuring instrument is a sensor-tipped guide wire.

Further according to the invention, the first flow measuring system and/or the second flow measuring system and/or the flow measurement device may be a system configured for measuring blood flow (or a flow substitute) by any invasive or non-invasive flow measurement technique. Invasive techniques may utilize e.g. continuous thermodilution or bolus thermodilution, timed venous collection, electromagnetic flow measurement, conductance measurements, Doppler ultrasound, or calibrated Doppler probes, thermoconvection, thermocondution, or epicardial ultrasonic flow velocity measurement. Non-invasive techniques for measuring blood flow (or a flow substitute) may be (but not limited to) Computed Tomography, Magnetic Resonance Imaging, Positron Emission Tomography, or echocardiography.

In an embodiment of the method according to the first aspect of the invention, the steps of measuring $Q_{rest}$, $P_a$, $Q_{max}$, and $P_{d, hyper}$ are omitted and are replaced by the following steps:
  determining the blood flow, $Q_{rest}$, through the coronary artery during rest condition of the patient;
  determining the blood pressure, $P_{a,rest}$, at a position proximal in the coronary artery or proximally of any stenosis if present during rest condition of the patient;
  determining the blood flow, $Q_{max}$, through the coronary artery during max hypermia of the patient; and
  determining the blood pressure, $P_{d, hyper}$, at a position distal in the coronary artery or distally of any stenosis if present during max hypermia of the patient, wherein the MRR, is calculated as $$MRR = \frac{Q_{max}}{Q_{rest}} \frac{P_{a,rest}}{P_{d,hyper}}.$$

In an embodiment of the system according to the second aspect of the invention, the first and second flow measuring systems and the first and second pressure measuring instruments are not part of the system, and the system instead comprises an interface, which interface may be integrally formed with the processing unit. The processing unit is configured to, in response to at least one signal received via said interface comprising data indicative of $Q_{rest}$, $P_{a, rest}$, $Q_{max}$, and $P_d$, hyper, determine the microvascular resistance reserve as $$MRR = \frac{Q_{max}}{Q_{rest}} \frac{P_{a,rest}}{P_{d,hyper}}.$$

The present invention also relates to a data processing device, a computer program product and a computer-readable storage medium that serve to carry out the inventive method in order to display measured and calculated values and, optionally, to guide a doctor during measurements and calculation of microvascular resistance reserve.

According to a third aspect of the invention, a method for determining microvascular resistance reserve, MRR, in the myocardium perfused by a normal or a stenotic coronary artery of a human patient is provided. The method comprises determining a value of Coronary Flow Reserve, CFR, of the coronary artery of the patient, determining a value of Fractional Flow Reserve, FFR, of the coronary artery of the patient, determining a value of blood pressure during rest condition of the patient, $P_{a, rest}$, at a position proximal in the coronary artery or proximally of any stenosis if present, determining a value of blood pressure during maximum hyperemia of the patient, $P_{a, hyper}$, at a position proximal in the coronary artery or proximally of any stenosis if present, wherein MRR is determined by calculating $$MRR = \frac{CFR}{FFR} \frac{P_{a,rest}}{P_{a,hyper}}.$$

It is understood that the steps of determining CFR, FFR, $P_{a, rest}$ and $P_{a, hyper}$ do not necessarily comprise conducting measurements, but may on the contrary solely comprise obtaining one or more previously calculated or measured values of CFR, FFR, $P_{a, rest}$ and/or $P_{a, hyper}$ In embodiments, the step of determining a value of CFR comprises measuring, during rest condition of the patient, blood flow, $Q_{rest}$, through the coronary artery, and measuring, during maximum hyperemia of the patient, blood flow, $Q_{max}$, through the coronary artery, wherein CFR is determined by calculating $CFR=Q_{max}/Q_{rest}$. The step of determining a value of CFR may comprise conducting at least one measurement using a non-invasive technique such as Computed Tomography, Magnetic Resonance Imaging, Positron Emission Tomography, or echocardiography to estimate the blood flows $Q_{max}$ and $Q_{rest}$. Alternatively, the step of determining a value of CFR the blood flows $Q_{max}$ and $Q_{rest}$ by means of an invasive method such as continuous thermodilution.

In embodiments, the step of determining a value of blood pressure during rest condition of the patient, $P_{a, rest}$, at a position proximal in the coronary artery or proximally of any stenosis if present comprises measuring blood pressure substantially simultaneously with the step of determining a value of CFR. For example, $P_{a, rest}$ may be measured during the same exam as the non-invasive flow measurements performed to determine CFR by means of a sphygmomanometer ("cuff measurement").

In embodiments, the step of determining a value of FFR comprises, during maximum hypermia of the patient measuring blood pressure, $P_{a, hyper}$, at a position proximal in the coronary artery or proximally of any stenosis if present and measuring blood pressure, $P_{d, hyper}$, at a position distal in the coronary artery or distally of any stenosis if present. FFR is calculated as FFR=$P_{d, hyper}$/$P_{a, hyper}$. The step of determining a value of FFR may comprise conducting at least one measurement using an invasive technique such as a pressure or guiding catheter or a sensor-tipped guide wire, i.e. $P_{a, hyper}$ and $P_{d, hyper}$ are measured invasively. Alternatively, step of determining a value of FFR may comprises conducting at least one measurement using a non-invasive technique such as Computed Tomography.

In embodiments, the measurements conducted to obtain a value of CFR and to obtain a value of FFR are performed at different times. For example, CFR can be obtained during a first exam, and FFR can be obtained during a separate second exam, such as an invasive cardiac catheterization performed at a different time or by noninvasive FFR determination (by means of CT for example). In such case, the knowledge that FFR is constant and not depending on the moment when it is measured, enables combination of (separately assessed) FFR (whether invasively by a pressure wire or non-invasively by CT) and the respective flow measurements determined non-invasely measured at another moment) and this provides MMR.

According to a fourth aspect of the invention, a method for determining microvascular resistance at rest condition, $R_{micro,rest}$, in the myocardium perfused by a normal or a stenotic coronary artery of a human patient is provided. The method comprises, during rest condition of the patient measuring blood flow, $Q_{rest}$, through the coronary artery, and measuring blood pressure, $P_{a, rest}$, at a position proximal in the coronary artery or proximally of any stenosis if present, wherein the microvascular resistance at rest condition is calculated as $R_{micro,rest}$=$P_{a, rest}$/$Q_{rest}$. The measuring of $Q_{rest}$ may be conducted using a non-invasive technique such as Computed Tomography, and the measuring of $P_{a, rest}$ may be conducted using a non-invasive technique such as using a sphygmomanometer.

According to a fifth aspect of the invention, a system for determining microvascular resistance reserve, MRR, in the myocardium perfused by a normal or a stenotic coronary artery of a human patient is provided. The system comprises a processing unit and an interface, which interface may be integrally formed with the processing unit. The processing unit is configured to, in response to at least one signal received via said interface comprising data indicative of the Coronary Flow Reserve, CFR, and the Fractional Flow Reserve, FFR, of the coronary artery of the patient, and further indicative of the blood pressure, $P_{a, rest}$, during rest condition of the patient at a position proximal in the coronary artery or proximally of any stenosis if present, and of the blood pressure, $P_{a, hyper}$, during maximum hyperemia of the patient at a position proximal in the coronary artery or proximally of any stenosis if present, determine the microvascular resistance reserve as $$MRR = \frac{CFR}{FFR} \frac{P_{a,rest}}{P_{a,hyper}}.$$

In other words, the processing unit is configured to receive values of i) Coronary Flow Reserve, CFR, of the coronary artery of the patient, ii) Fractional Flow Reserve, FFR, of the coronary artery of the patient, iii) blood pressure during rest condition of the patient, $P_{a, rest}$, at a position proximal in the coronary artery or proximally of any stenosis if present, and iv) blood pressure during maximum hyperemia of the patient, $P_{a, hyper}$, at a position proximal in the coronary artery or proximally of any stenosis if present. It is understood that these values do not necessarily need to be measured by measurement devices being part of the system but may on the contrary be measured by one or more measurement devices connected directly or indirectly to the interface. Alternatively, the values may be previously calculated or measured values of CFR, FFR, $P_{a, rest}$ and/or $P_{a, hyper}$ which may be stored on a storage device connected to the interface.

In embodiments of the fifth aspect of the invention, the system comprises a flow measuring device configured for measuring the blood flow, $Q_{rest}$, through the coronary artery during rest condition of the patient and for measuring the blood flow, $Q_{max}$, through the coronary artery during maximum hyperemia of the patient. The flow measuring device is connected directly or indirectly to the interface, and the at least one signal received by the processing unit via said interface comprising data indicative of the CFR comprises values of $Q_{rest}$ and $Q_{max}$ from said flow measuring device, wherein the processing unit is configured to calculate CFR=$Q_{max}$/$Q_{rest}$. The flow measuring device may comprise first and second flow measuring systems in the same manner as described above with reference to the second aspect of the invention.

In embodiments of the fifth aspect of the invention, the system comprises a pressure measuring device configured for measuring the blood pressure, $P_{a, hyper}$, at a position proximal in the coronary artery or proximally of any stenosis, if present, during maximum hyperemia of the patient, and for measuring the blood pressure, $P_{d, hyper}$, at a position distal in the coronary artery or distally of any stenosis, if present, during maximum hyperemia of the patient. The pressure measuring device is connected directly or indirectly to the interface, and the at least one signal received by the processing unit via said interface comprising data indicative of the FFR comprises values of $P_{a, hyper}$ and $P_{d, hyper}$ from said flow measuring arrangement, wherein the processing unit is configured to calculate FFR=$P_{d, hyper}$/$P_{a, hyp}$er. The pressure measuring device may comprise first and second pressure measuring instruments, or embodiments thereof, in the same manner as described above with reference to the second aspect of the invention.

According to a sixth aspect of the invention, there is provided a system for determining microvascular resistance, $R_{micro,rest}$, at rest condition in the myocardium perfused by a normal or a stenotic coronary artery of a human patient. The system comprises a processing unit and an interface, wherein said processing unit is configured to, in response to at least one signal received via said interface comprising data indicative of the blood flow, $Q_{rest}$, through the coronary artery during rest condition of the patient and of the blood pressure, $P_{a, rest}$, at a position proximal in the coronary artery or proximally of any stenosis if present during rest condition of the patient, determine the microvascular resistance at rest condition as $R_{micro,rest}$=$P_{a, rest}$/$Q_{rest}$.

In other words, the processing unit is configured to receive values of i) blood pressure during rest condition of the patient, $P_{a, rest}$, at a position proximal in the coronary artery or proximally of any stenosis if present, and ii) blood flow, $Q_{rest}$, through the coronary artery during rest condition of the patient. It is understood that these values do not necessarily need to be measured by measurement devices being part of the system but may on the contrary be measured by one or more measurement devices connected directly or indirectly to the interface. Alternatively, the values may be previously measured values $P_{a, rest}$ and $Q_{rest}$ which may be stored on a storage device connected to the interface.

In embodiments of the sixth aspect of the invention, the system comprises a flow measuring device configured for measuring the blood flow, $Q_{rest}$, through the coronary artery during rest condition of the patient. The flow measuring device is connected directly or indirectly to the interface, and the at least one signal received by the processing unit via said interface comprising data indicative of $Q_{rest}$. The flow measuring device may comprise a first or second flow measuring system in the same manner as described above with reference to the second aspect of the invention. Furthermore, the system may comprise a pressure measuring device configured for measuring the blood pressure, $P_{a, rest}$, at a position proximal in the coronary artery or proximally of any stenosis, if present, during rest of the patient. The pressure measuring device is connected directly or indirectly to the interface, and the at least one signal received by the processing unit via said interface comprising data indicative of $P_{a, rest}$ from said flow measuring arrangement. The pressure measuring device may comprise a first or second pressure measuring instruments in the same manner as described above with reference to the second aspect of the invention. In a particularly advantageous embodiment of the sixth aspect of the invention, the system comprises a Computed Tomography or PET or MRI system for estimating $Q_{rest}$, and a sphygmomanometer for measuring $P_{a, rest}$.

The features of the embodiments described above are combinable in any practically realizable way to form embodiments having combinations of these features. Further, all features and advantages of embodiments described above with reference to the first, second, third, fourth, fifth and sixth aspects of the invention may be applied in corresponding embodiments of any of the other aspects of the invention.

BRIEF DESCRIPTION OF THE DRAWINGS

Above discussed and other aspects of the present invention will now be described in more detail using the appended drawings, wherein.

DETAILED DESCRIPTION

Figure 1:
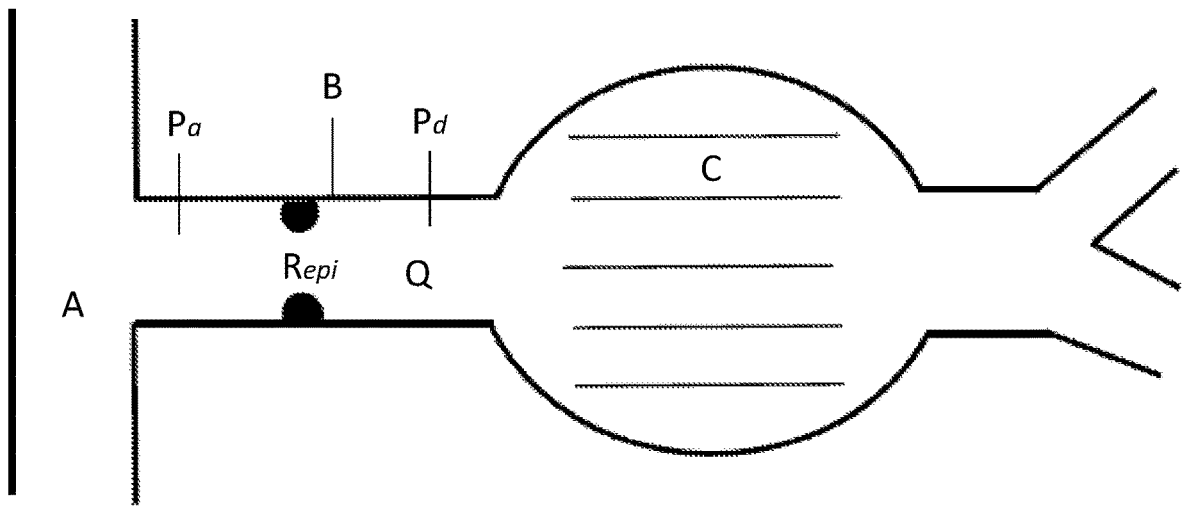
FIG. 1 illustrates schematically the coronary circulation.

In FIG. 1, the letter A indicates the aorta, the letter B indicates the epicardial artery, and the letter C indicates the microcirculation; and, further, $P_a$ is the pressure proximally of a stenosis and $P_d$ is the pressure distally of the stenosis, and $R_{epi}$ is the resistance of the stenosis. In a normal, non-stenotic vessel $R_{epi}=0$, and $P_a=P_d$. Then, during rest condition of the patient, the microvascular resistance can be written as:

$$R_{micro,rest,N} = P_{a,rest}/Q_{rest,N}$$

(where the suffix "N" indicates a completely normal coronary artery) or simply $$R_{micro,rest} = P_{a,rest}/Q_{rest}$$

In the presence of an epicardial disease, $R_{epi}>0$, and the epicardial disease can be focal but also diffuse. The microvascular resistance in this stenotic case can, during rest condition of the patient, be written as:

$$R_{micro,rest,sten} = P_{d,rest}/Q_{rest,sten}$$

(where the suffix "sten" indicates the presence of a stenosis).

One may note that $R_{micro,rest,sten} < R_{micro,rest,N}$ because the presence of $R_{epi}$ induces an equivalent compensatory decrease of $R_{micro,rest,N}$ in order to keep resting blood flow ($Q_{rest}$) constant (autoregulatory response of the coronary circulation). Therefore $R_{micro,rest,sten}$ can also be written as:

$$R_{micro,rest,sten} = R_{micor,rest,N} - R_{epi} \text{ or}$$

$$R_{micro,rest,N} = R_{micro,rest,sten} + R_{epi}$$

$$= \frac{P_{d,rest}}{Q_{rest,sten}} + \frac{P_{a,rest} - P_{d,rest}}{Q_{rest,sten}}$$

$$= P_{a,rest}/Q_{rest,sten}$$

However, since $Q_{rest,sten} = Q_{rest,N}$, this can be rewritten as:

$$R_{micro,rest} = P_{a,rest}/Q_{rest} \tag{1}$$

The pressure $P_{a, rest}$, which is the pressure measured proximally of the stenosis, can preferably be measured as the aortic pressure and can be measured at the entrance of the coronary artery, and can then be measured with a so-called guiding or pressure catheter, and $Q_{rest}$ is the measured resting blood flow, which can be measured with a thermodilution technique; or the blood flow can be measured or estimated with any other suitable invasive or non-invasive technique as will be discussed below. It can further be noted that Equation (1) for calculating the microvascular resistance at rest is universally valid and is not dependent on presence or absence of an epicardial disease.

The equations above were derived for rest condition. During hyperemic conditions of the patient, i.e. when the microvascular resistance is at a minimum and the blood flow is at a maximum, we have for a normal, non-stenotic vessel $P_{a, hyper} = P_{d, hyper}$, and:

$$R_{micro,min,N} = P_{a,hyper}/Q_{max,N}$$

Or simply $$R_{micro,min} = P_{a,hyper}/Q_{max}$$

In the presence of an epicardial disease, which can be focal or diffuse, there is an additional resistance $R_{epi}$, and during hyperemia, when the microvascular resistance is at a minimum and the blood flow is at a maximum, then:

$$R_{micro,min,sten} = P_{d,hyper}/Q_{max,sten} \tag{2b}$$

and because $R_{micro,min,sten}=R_{micro,min,N}$, Equation (2b) can be written as:

$$R_{micro,min}=P_{d,hyper}/Q_{max} \tag{2}$$

where $P_{d,\,hyper}$ is the distal coronary pressure as measured distally of a stenosis during hyperemic conditions of the patient, and where the blood flow $Q_{max}$ is simultaneously measured by thermodilution or by any other suitable invasive or non-invasive method for measuring blood flow during hyperemia.

Microvascular resistance reserve (MRR) is a novel quantity within the field of coronary medicine; and despite its apparent usefulness it has never before been measured and calculated in absolute terms. The microvascular resistance reserve (MRR) is defined as:

$$MRR = \frac{R_{micro,rest}}{R_{micro,min}}$$

(with $R_{micro,rest}$ as not confounded by epicardial disease) which by substituting $R_{micro,rest}$ with Equation (1) and $R_{micro,min}$ with Equation (2) can be written as:

$$MRR = \frac{Q_{max}}{Q_{rest}} \frac{P_{a,rest}}{P_{d,hyper}} \tag{3}$$

with $P_{a,\,rest}$ measured at rest and $P_{d,\,hyper}$ measured at hyperemia

It can be noted that MRR as defined above is a universally valid value of microvascular resistance reserve (MRR) and is independent of the presence or absence of an epicardial disease.

This latter property is a unique feature of this novel index.

Figure 2:
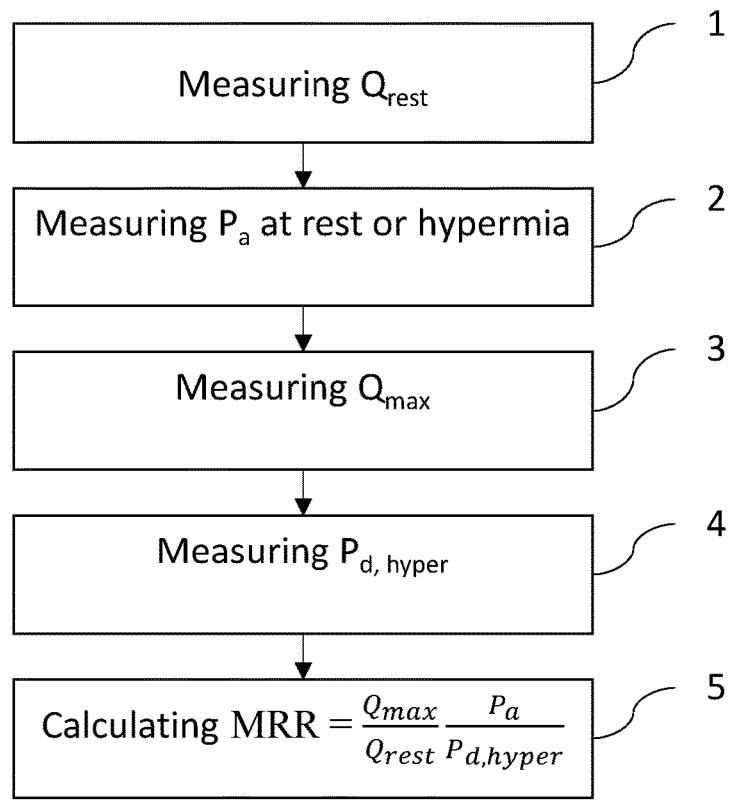
FIG. 2 shows a flow chart of an embodiment of the method according to the first aspect of the invention.

FIG. 2 shows a flow chart of an embodiment of the method according to the first aspect of the invention. The method comprises measuring 1 blood flow, $Q_{rest}$, through the coronary artery; and further comprising the step of during rest condition or during maximum hyperemia of the patient measuring 2 blood pressure, $P_a$, at a position proximal in the coronary artery or proximally of any stenosis if present. The method further comprises the steps of during maximum hyperemia of the patient measuring 3 blood flow, $Q_{max}$, through the coronary artery; and measuring 4 blood pressure, $P_{d,hyper}$, at a position distal in the coronary artery or distally of any stenosis if present. The microvascular resistance reserve is determined by the additional step of calculating 5 the microvascular resistance reserve as $$MRR = \frac{Q_{max}}{Q_{rest}} \frac{P_a}{P_{d,hyper}}$$

The pressure measurements required by the present method are all well known to the skilled person and are in particular practiced during measurement of the fractional flow reserve (FFR), which is a standard technique in medical examinations of the coronary artery. During FFR measurements the presence and the position of a stenosis, if any, are determined. Typically, the measurement distally of a stenosis (or distal in the coronary artery if no stenosis is present) is performed with a sensor-tipped guidewire. Such sensors are readily available, e.g. the PressureWire™ X Guidewire sold by the company Abbott. The pressure proximally can be measured with a so-called pressure catheter or guiding catheter. It is, however, possible to also measure the proximal pressure with a sensor-tipped guidewire. Here it should be noted that from experience it is known that aortic pressure is generally independent of the state of the patient (i.e. whether the patient is in a state of hyperemia or in rest) if blood flow, both at rest and at hyperemia, is measured by thermodilution flow measurements and saline is continuously infused at different infusion rates. Thus, according to the present invention, the proximal pressure can be measured then during rest condition of the patient or during hyperemic state of the patient. Thus, equation (3) derived above can be generalized as:

$$MRR = \frac{Q_{max}}{Q_{rest}} \frac{P_a}{P_{d,hyper}} \tag{3b}$$

In case that $P_a$ does change between the state of rest and the state of hyperemia (as can be the case with other means to induce hyperemia such as—but not limited to—adenosine injection or infusion), it is important that the pressure measured proximally of the stenosis should be taken as $P_a$ at rest (also called $P_{a,rest}$) and $P_d$ as $P_d$ during hyperemia (also called $P_{d,hyper}$), see equation (3). The skilled person is further very familiar with methods for inducing a hyperemic state in a patient.

The flow measurements and the corresponding flow measurement system(s) for performing such flow measurements can, for example, by done with a system for measuring blood flow according to the continuous thermodilution technique. This is a technique well known to the skilled person, and is, for example, described in the U.S. Pat. No. 7,775,988 to Pijls. A catheter for such flow measurements is also readily available, for example the RayFlow™ multipurpose infusion catheter sold by the company HexaCath.

However, the skilled person knows many other techniques for invasive or non-invasive blood flow measurements. Such invasive techniques encompass bolus thermodilution, timed venous collection, electromagnetic flow measurement, conductance measurements, Doppler ultrasound, or calibrated Doppler probes, thermo-convection, thermo-conduction, and epicardial ultrasonic flow velocity measurement. Most of these techniques are, for example, described in "Maximal Myocardial Perfusion as a Measure of the Functional Significance of Coronary Artery Disease", by N. H. J. Pijls (1991), Cip-Gegevens Koninklijke Bibliotheek, den Haag, (ISBN 90-9003818-3). Examples of non-invasive flow measurement are techniques using Computed Tomography, Magnetic Resonance Imaging, Positron Emission Tomography, or echocardiography Typically, the system for blood flow measurement during rest condition of the patient is the same as the system for blood flow measurement during a hyperemic state of the patient. It is, however, within the scope of the invention, that a first blood flow measuring system, which is used for blood flow measurement during rest condition, is different from a second blood flow measuring system, which is used for blood flow measurements during hyperemic condition. It is also within the scope of the invention that $Q_{max}$ and $Q_{rest}$ and $P_a$ and $P_d$ can be measured at different times.

Figure 3:
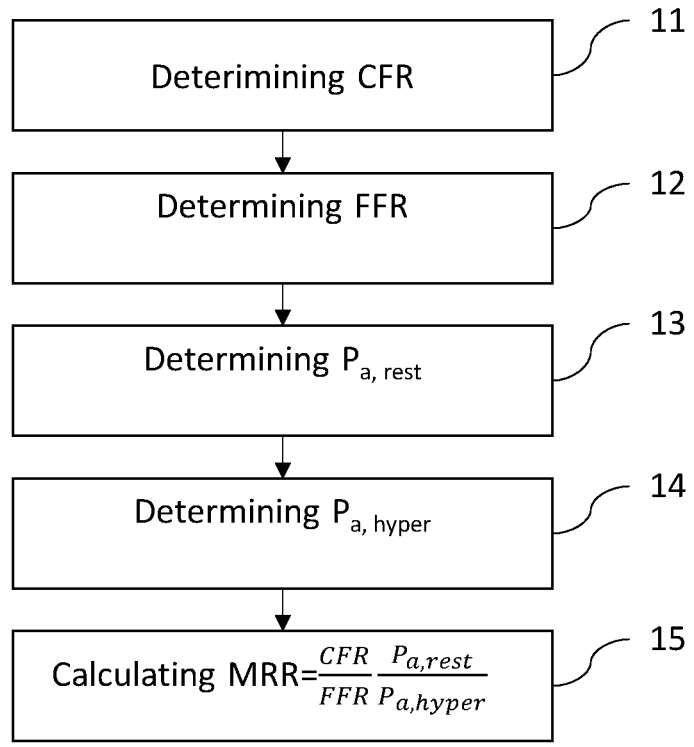
FIG. 3 shows a flow chart of an embodiment of the method according to the third aspect of the invention.

FIG. 3 shows a flow chart of an embodiment of the method according to the third aspect of the invention, which method is an alternative method of determining MRR, but will result in, at least theoretically, identical values of MRR as the method according to the first aspect of the invention. This is understood by re-arranging equation (3) as follows:

$$P_{a,rest}/P_{d,hyper} = (P_{a,rest}/P_{a,hyper}) \cdot (P_{a,hyper}/P_{d,hyper})$$

One gets: $MRR = Q_{max}/Q_{rest} \times (P_{a,rest}/P_{a,hyper}) \cdot (P_{a,hyper}/P_{d,hyper})$ Which equation makes clear that MRR contains a term ($P_{a,\ rest}/P_{a,\ hyper}$) to compensate for changes in driving pressure $P_a$ between the resting and hyperemic measurement and contains a term ($P_{a,\ hyper}/P_{d,\ hyper} = 1/FFR$) to compensate for presence of any kind of epicardial disease.

This can be re-written then as:

$$MRR = (CFR/FFR) \cdot (P_{a,rest}/P_{a,hyper}) \quad (4)$$

or simply MRR=(CFR/FFR) if $P_a$ remains constant between resting conditions and hyperemia. Equation (4) gives the mutual relationship between MRR, CFR and FFR and is universally valid in coronary physiology. Furthermore, equation (4) is not dependent on the technique used to obtain CFR and FFR.

The method in FIG. 3 comprises the determining 11 a value of Coronary Flow Reserve, CFR, of the coronary artery of the patient, determining 12 a value of Fractional Flow Reserve, FFR, of the coronary artery of the patient, determining 13 a value of blood pressure during rest condition of the patient, $P_{a,\ rest}$, at a position proximal in the coronary artery or proximally of any stenosis if present, determining 14 a value of blood pressure during maximum hyperemia of the patient, $P_{a,\ hyper}$, at a position proximal in the coronary artery or proximally of any stenosis if present. The microvascular resistance reserve, MRR, is determined by the additional step of calculating 15 the microvascular resistance reserve according to equation (4).

Figure 4:
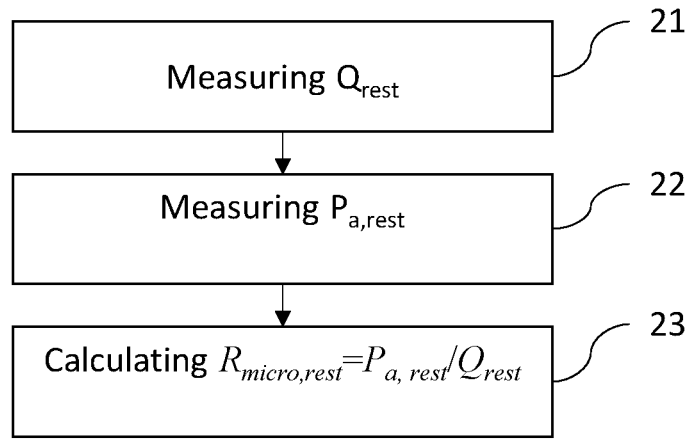
FIG. 4 shows a flow chart of an embodiment of the method according to the third aspect of the invention.

FIG. 4 shows a flow chart of an embodiment of the method according to the third aspect of the invention. The method relates to determining microvascular resistance as defined in equation (2). The method comprises, during rest condition of the patient, measuring 21 blood flow, $Q_{rest}$, through the coronary artery, and measuring 22 blood pressure, $P_{a,\ rest}$, at a position proximal in the coronary artery or proximally of any stenosis if present. The microvascular resistance at rest condition is calculated 23 as $R_{micro,rest} = P_{a,\ rest}/Q_{rest}$.

Figure 5:
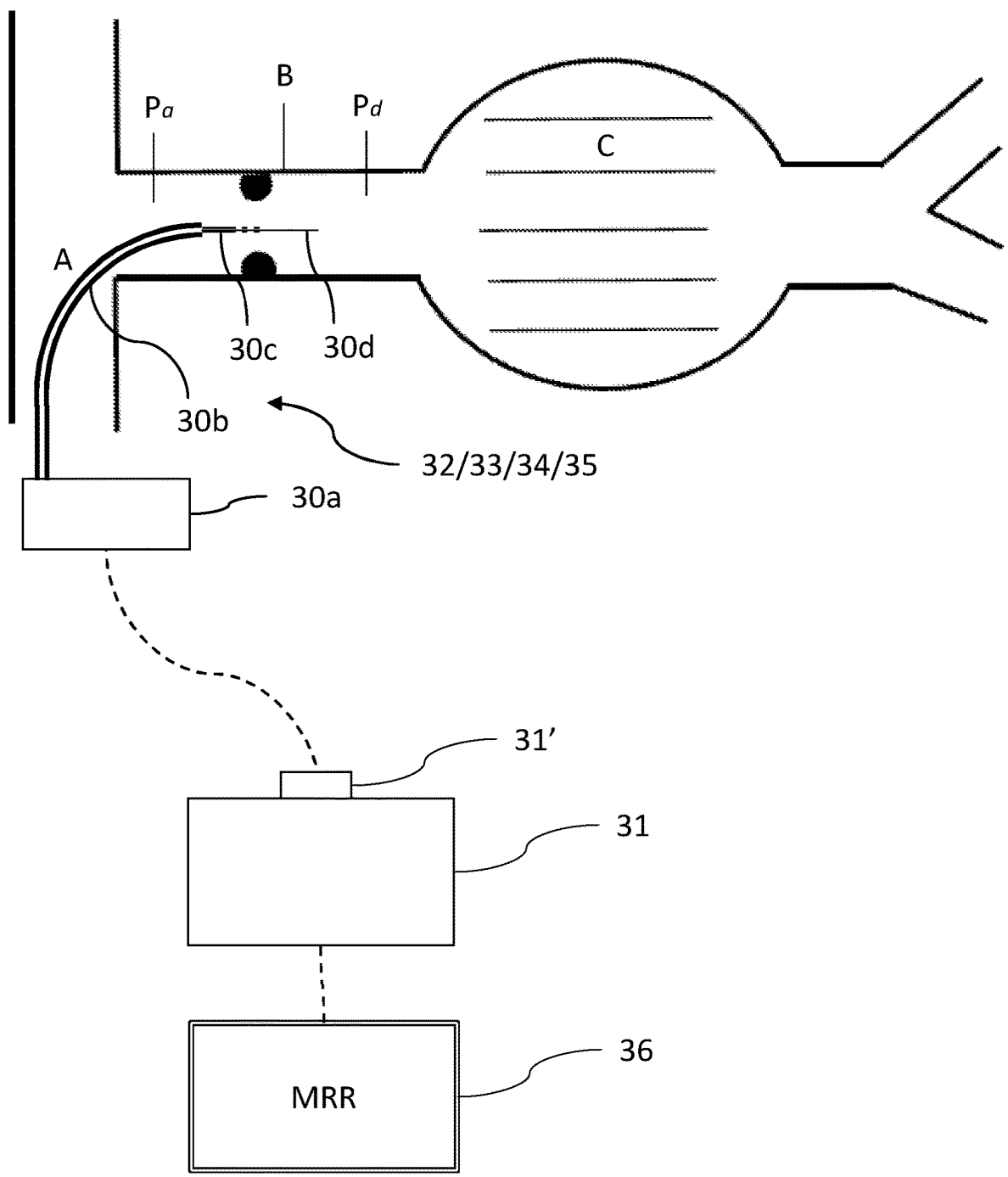
FIG. 5 illustrates schematically a system according to the second aspect of the invention.

FIG. 5 illustrates schematically a system according to the second aspect of the invention. The system comprises a processing unit 31 and a measuring system 32/33/34/35 using the continuous thermodilution principle. The measuring system comprises a control unit 30a, guide catheter 30b, infusion catheter 30c and a sensor 30d arranged on a sensor guide wire. As noted above, such a system is known in the art and will not be described in further detail here. The sensor 30d is configured to measure temperature and pressure. In the shown position, the measuring system can measure $Q_{rest}$, $Q_{max}$, $P_{d,hyper}$, and by repositioning the sensor to a proximal position, Pa can be measured as well. The measuring system thus constitutes the first and second flow measuring systems as well as the first and second pressure measuring instruments in the sense of the second aspect of the invention. In other embodiments, $P_a$ may however be measured by means of a separate measuring device (such as a guide catheter), or different type(s) of measuring system(s) may be used altogether. The control unit 30a is electrically connected to the processing unit 31 via its interface 31', such that the processing unit can obtaining blood flow measurements $Q_{rest}$, $Q_{max}$ and blood pressure measurements $P_a$, $P_d$ from the measuring system. The processing unit 31 is configured for calculating the microvascular resistance reserve as $$MRR = \frac{Q_{max}}{Q_{rest}} \frac{P_a}{P_{d,hyper}}.$$

In this embodiment, the system comprises a display unit 36 which is electrically connected to the processing unit 31 and on which the measured and/or calculated values MRR, $Q_{rest}$, $Q_{max}$ and/or $P_a$, $P_d$ can be displayed in, preferably, real time.

Figure 6:
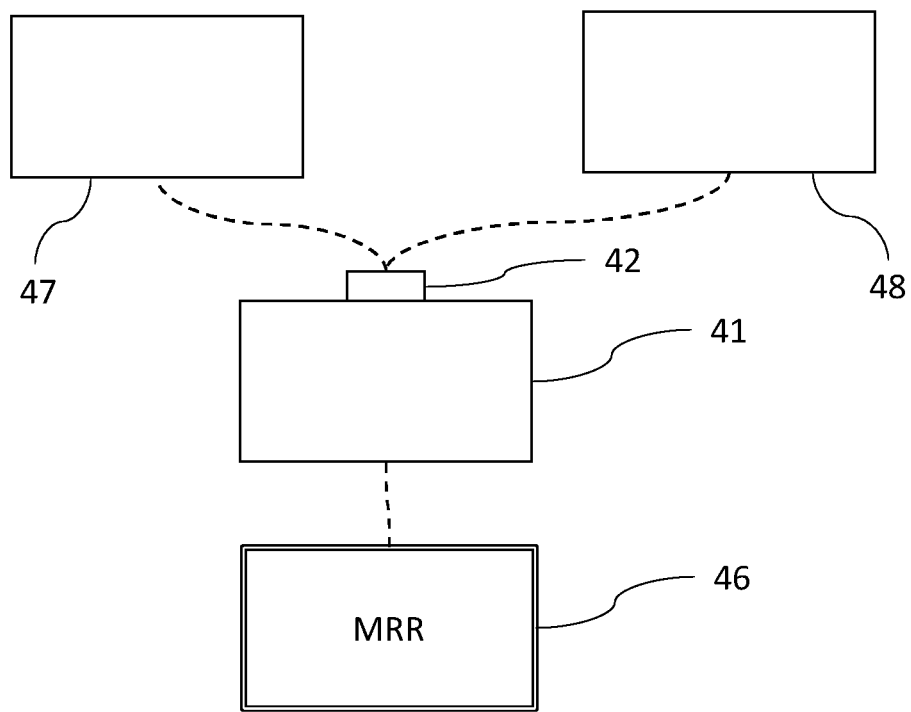
FIG. 6 illustrates schematically a system according to the fifth aspect of the invention.

FIG. 6 illustrates schematically a system according to the fifth aspect of the invention. The system comprises a processing unit 41 and an interface 42. The processing unit is configured to, in response to at least one signal received via said interface comprising data indicative of the Coronary Flow Reserve, CFR, and the Fractional Flow Reserve, FFR, of the coronary artery of the patient, of the, of the coronary artery of the patient, and further indicative of the blood pressure, $P_{a,\ rest}$, during rest condition of the patient at a position proximal in the coronary artery or proximally of any stenosis if present, and of the blood pressure, $P_{a,\ hyper}$, during maximum hyperemia of the patient at a position proximal in the coronary artery or proximally of any stenosis if present, determine the microvascular resistance reserve as $$MRR = \frac{CFR}{FFR} \frac{P_{a,rest}}{P_{a,hyper}}.$$

The system comprises a display unit 56 which is electrically connected to the processing unit 41 and on which the values of MRR, CFR and/or FFR may be displayed in, preferably, real time. A CT system 47 and a pressure measurement device 48 (a sphygmomanometer) is connected to the interface to provide data for determining CFR, FFR and MRR. The system may in other embodiments comprise a measuring system as shown in FIG. 5 connected to the interface 42. In yet other embodiments, a data storage device comprising stored values of CFR, FFR, $P_{a,\ rest}$, $P_{a,\ hyper}$ may be connected to the interface.

Figure 7:
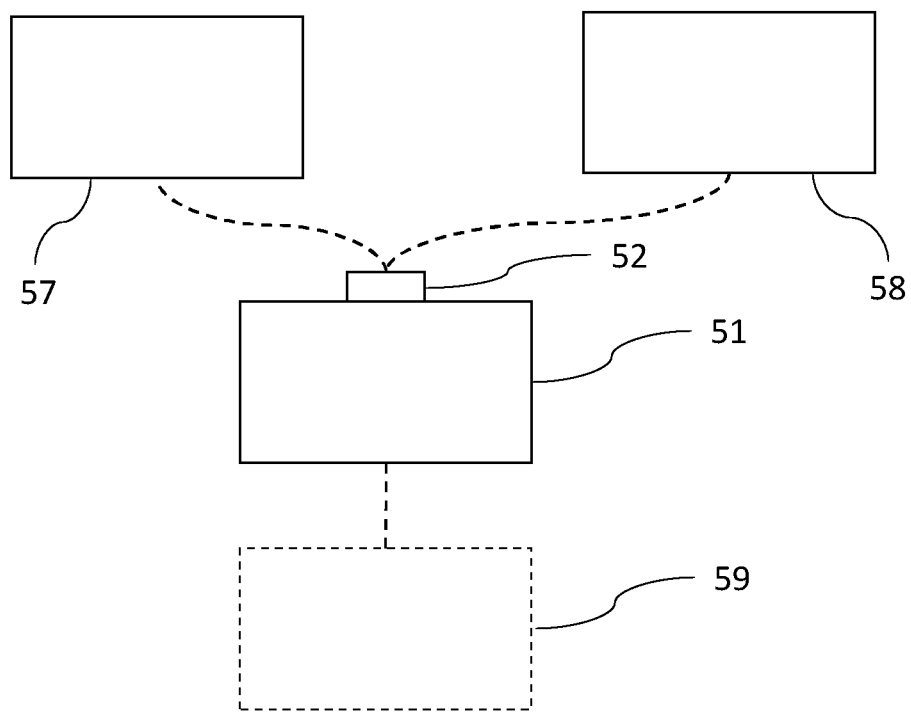
FIG. 7 illustrates schematically a system according to the sixth aspect of the invention.

FIG. 7 illustrates schematically a system according to the sixth aspect of the invention. The system comprises a processing unit 51 and a thereto connected interface 52, wherein said processing unit is configured to, in response to at least one signal received via said interface comprising data indicative of the blood flow, $Q_{rest}$, through the coronary artery during rest condition of the patient and of the blood pressure, $P_{a,\ rest}$, at a position proximal in the coronary artery or proximally of any stenosis if present during rest condition of the patient, determine the microvascular resistance at rest condition as $R_{micro,rest} = P_{a,\ rest}/Q_{rest}$. A CT system 57 and a pressure measurement device 58 (a sphygmomanometer) is connected to the interface to provide data indicative of $Q_{rest}$, and $P_{a,\ rest}$. In this embodiment, no display is provided. Instead, an optional wireless communications module is shown connected to the processing unit to communicate the calculated microvascular resistance. The processing unit configured to calculate $R_{micro,rest}$ may in other embodiments be part of the CT system. In other embodiments, the system 57 may be a PET or MRI system.

As described above, the systems according to the invention comprise a processing unit, which may obtains signals or other quantities from for example the first and second flow measuring systems and the first and second pressure measuring instruments, respectively, and which transforms these signals or other quantities into value(s) or number(s), which can be at least temporarily stored and used to calculate the resting and minimal microvascular resistance and the microvascular resistance reserve (MRR) in accordance with the invention. According to embodiments, the systems comprise a display unit, on which the measured and/or calculated values can be displayed in, preferably, real time.

As said, embodiments of the invention described above comprise a processing unit, in which processes are performed in at least one processor, the invention also extends to computer programs, particularly computer programs on or in a carrier, adapted for putting the invention into practice. The programs may be in the form of source code, object code, a code intermediate source and object code such as in partially compiled form, comprise software or firmware, or in any other form suitable for use in the implementation of the process according to the invention. The program may either be a part of an operating system, or be a separate application. The carrier may be any entity or device capable of carrying the program. For example, the carrier may comprise a storage medium, such as a Flash memory, a ROM (Read Only Memory), for example a DVD (Digital Video/Versatile Disk), a CD (Compact Disc) or a semiconductor ROM, an EPROM (Erasable Programmable Read-Only Memory), an EEPROM (Electrically Erasable Programmable Read-only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant processes. In one or more embodiments, there may be provided a computer program loadable into a memory communicatively connected or coupled to at least one data processor, e.g. the processing unit, comprising software or hardware for executing the method according any of the embodiments herein when the program is run on the at least one data processor. In one or more further embodiment, there may be provided a processor-readable medium, having a program recorded thereon, where the program is to make at least one data processor, e.g. the processing unit, execute the method according to of any of the embodiments herein when the program is loaded into the at least one data processor.

Although the present invention has been described with reference to specific embodiments, also shown in the appended drawings, it will be apparent to those skilled in the art that many variations and modifications can be done within the scope of the invention as described in the specification and defined with reference to the claims below.

What is claimed is:

1. A method for determining microvascular resistance reserve, MRR, in the myocardium perfused by a normal or a stenotic coronary artery of a human patient, which method comprises the step of during rest condition of the patient:
measuring blood flow, $Q_{rest}$, through the coronary artery; and
further comprising the step of during rest condition or during maximum hyperemia of the patient:
measuring blood pressure, $P_a$, at a position proximal in the coronary artery or proximally of any stenosis if present; and
further comprising the steps of during maximum hyperemia of the patient:
measuring blood flow, $Q_{max}$, through the coronary artery; and
measuring blood pressure, $P_{d,hyper}$, at a position distal in the coronary artery or distally of any stenosis if present, wherein the microvascular resistance reserve is determined by the additional step of calculating the microvascular resistance reserve as $$MRR = \frac{Q_{max}}{Q_{rest}} \frac{P_a}{P_{d,hyper}}.$$

2. The method according to claim 1, wherein the step of measuring the blood pressure, $P_a$, at a position proximal in the coronary artery or proximally of any stenosis, if present, comprises the step of measuring the aortic blood pressure.

3. The method according to claim 1, wherein the step of measuring the blood pressure at a position proximal in the coronary artery or proximally of any stenosis, if present, is performed during rest condition of the patient.

4. The method according to claim 3, further comprising calculating microvascular resistance, $R_{micro,rest}$, at rest condition of the patient as $R_{micro,rest} = P_{a,rest}/Q_{rest}$.

5. A method for determining microvascular resistance reserve, MRR, in the myocardium perfused by a normal or a stenotic coronary artery of a human patient, which method comprises:
determining a value of Coronary Flow Reserve, CFR, of the coronary artery of the patient;
determining a value of Fractional Flow Reserve, FFR, of the coronary artery of the patient;
determining a value of blood pressure during rest condition of the patient, $P_{a, rest}$, at a position proximal in the coronary artery or proximally of any stenosis if present; and
determining a value of blood pressure during maximum hyperemia of the patient, $P_{a, hyper}$, at a position proximal in the coronary artery or proximally of any stenosis if present,
wherein the microvascular resistance reserve, MRR, is determined by the additional step of calculating the microvascular resistance reserve as $$MRR = \frac{CFR}{FFR} \frac{P_{a,rest}}{P_{a,hyper}}.$$

6. The method according to claim 5, wherein determining the value of CFR comprises:
measuring, during rest condition of the patient, blood flow, $Q_{rest}$, through the coronary artery; and
measuring, during maximum hyperemia of the patient, blood flow, $Q_{max}$, through the coronary artery,
wherein CFR is determined by calculating $CFR = Q_{max}/Q_{rest}$.

7. The method according to claim 6, wherein said determining the value of CFR comprises conducting at least one measurement using a non-invasive technique such as Computed Tomography, Magnetic Resonance Imaging, Positron Emission Tomography, or echocardiography.

8. The method according to claim 5, wherein determining the value of blood pressure during rest condition of the patient, $P_{a, rest}$, at a position proximal in the coronary artery or proximally of any stenosis if present comprises measuring blood pressure substantially simultaneously with the step of obtaining a value of CFR.

9. The method according to claim 5, wherein determining the value of FFR comprises, during maximum hypermia of the patient:
   measuring blood pressure, $P_{a,\,hyper}$, at a position proximal in the coronary artery or proximally of any stenosis if present; and
   measuring blood pressure, $P_{d,\,hyper}$, at a position distal in the coronary artery or distally of any stenosis if present,
   wherein FFR is calculated as $FFR=P_{d,\,hyper}/P_{a,\,hyper}$.

10. The method according to claim 9, wherein determining the value of FFR comprises conducting at least one measurement using an invasive technique such as a pressure or guiding catheter or a sensor-tipped guide wire.

11. The method according to claim 9, wherein determining the value of FFR comprises conducting at least one measurement using a non-invasive technique such as Computed Tomography.

12. The method according to claim 5, wherein measurements conducted to determine the value of CFR and to determine the value of FFR are performed at different times.

13. The method according to claim 5, wherein at least one of determining the value of CFR, determining the value of FFR, determining the value of $P_{a,rest}$ and determining the value of $P_{a,hyper}$ comprises obtaining a previously calculated or measured value.

14. A method for determining microvascular resistance at rest condition, $R_{micro,rest}$, in the myocardium perfused by a normal or a stenotic coronary artery of a human patient, which method comprises, during rest condition of the patient:
   measuring blood flow, $Q_{rest}$, through the coronary artery; and
   measuring blood pressure, $P_{a,\,rest}$, at a position proximal in the coronary artery or proximally of any stenosis if present,
wherein the microvascular resistance at rest condition is calculated by the additional step of calculating the microvascular resistance as $R_{micro,rest}=P_{a,rest}/Q_{rest}$.

15. The method according to claim 14, wherein said measuring $Q_{rest}$ is conducted using a non-invasive technique such as Computed Tomography, Magnetic Resonance Imaging or Positron Emission Tomography, and wherein said measuring $P_{a,\,rest}$ is conducted using a non-invasive technique such as using a sphygmomanometer.

16. A non-transitory computer readable medium comprising instructions which, when executed by a processing unit, cause the processing unit to carry out the method of claim 5.

17. A system for determining microvascular resistance reserve, MRR, in the myocardium perfused by a normal or a stenotic coronary artery of a human patient, comprising:
   a processing unit;
   a first flow measuring system configured for measuring the blood flow, $Q_{rest}$, through the coronary artery during rest condition of the patient;
   a first pressure measuring instrument configured for measuring the blood pressure, $P_a$, at a position proximal in the coronary artery or proximally of any stenosis, if present, during rest condition or during maximum hyperemia of the patient;
   a second flow measuring system configured for measuring the blood flow, $Q_{max}$, through the coronary artery during maximum hyperemia of the patient; and
   a second pressure measuring instrument configured for measuring the blood pressure, $P_{d,hyper}$, at a position distal in the coronary artery or distally of any stenosis, if present, during maximum hyperemia of the patient,
wherein the processing unit is configured for obtaining blood flow measurements $Q_{rest}$, $Q_{max}$ from the first and second flow measuring systems and obtaining blood pressure measurements $P_a$, $P_{d,\,hyper}$ from the first and second pressure measuring instruments, and wherein the processing unit is further configured for calculating the microvascular resistance reserve as $$MRR = \frac{Q_{max}}{Q_{rest}} \frac{P_a}{P_{d,hyper}}.$$

18. The system according to claim 17, wherein the first flow measuring system and the second flow measuring system are the same flow measuring system.

19. The system according to claim 17, wherein the system further comprises:
   a display unit configured for receiving the calculated value of the microvascular resistance reserve from the processing unit and displaying said calculated value.

20. The system according to claim 17, wherein the first pressure measuring instrument comprises a pressure catheter or a guiding catheter.

21. The system according to claim 17, wherein the first pressure measuring instrument and/or the second pressure measuring instrument comprises a sensor-tipped guide wire.

22. The system according to claim 17, wherein the first flow measuring system and/or the second flow measuring system is a system which utilizes a invasive or non-invasive flow or flow substitute measurement.

23. A system for determining microvascular resistance reserve, MRR, in the myocardium perfused by a normal or a stenotic coronary artery of a human patient, comprising:
   a processing unit;
   a first pressure measuring instrument configured for measuring blood pressure, $P_{a,rest}$ during rest condition of the patient at a position proximal in the coronary artery or proximally of any steno sis, if present;
   a second pressure measuring instrument configured for measuring blood pressure $P_{a,hyper}$, during maximum hyperemia of the patient at a position proximal in the coronary artery or proximally of any steno sis, if present;
   wherein said processing unit is configured for obtaining the blood pressure measurements $P_{a,rest}$, $P_{a,hyper}$ from the first and second pressure measuring instruments and obtaining at least one signal comprising data indicative of the Coronary How Reserve, CFR, and the Fractional Flow Reserve, FFR, of the coronary artery of the patient, and wherein the processing unit is further configured for calculating the microvascular resistance reserve as $$MRR = \frac{CFR}{FFR} \frac{P_{a,rest}}{P_{a,hyper}}.$$

24. A system for determining microvascular resistance, $R_{micro,rest,}$ at rest condition in the myocardium perfused by a normal or a stenotic coronary artery of a human patient, comprising:
   a processing unit;
   a flow measuring system configured for measuring blood flow, $Q_{rest}$, through the coronary artery during rest condition of the patient; and a pressure measuring instrument configured for measuring the blood pressure, $P_{a,rest}$, at a position proximal in the coronary artery or proximally of any stenosis, if present, during rest condition of the patient;

wherein said processing unit is configured for obtaining the blood measurement $Q_{rest}$ from the flow measuring system, and obtaining the blood pressure measurement $P_{a,rest}$ from the pressure measuring instrument, and wherein the processing unit is further configured for calculating the microvascular resistance at rest condition as $R_{micro,rest} = P_{a,rest}/Q_{rest}$.

* * * * *